(12) United States Patent
Srivastava et al.

(10) Patent No.: US 8,389,577 B2
(45) Date of Patent: Mar. 5, 2013

(54) METHOD OF TREATING A HUMAN BEING FOR A CLASS OF METABOLIC DEFECTS AND ENERGY PRODUCTION DISORDERS

(76) Inventors: Suresh C. Srivastava, Burlington, MA (US); Sant K. Srivastav, Burlington, MA (US); Stanley J. Szymanski, Jr., Sewickley, PA (US)

( * ) Notice: Subject to any disclaimer, the term of this patent is extended or adjusted under 35 U.S.C. 154(b) by 0 days.

(21) Appl. No.: 12/932,939

(22) Filed: Mar. 9, 2011

(65) Prior Publication Data

US 2011/0166231 A1 Jul. 7, 2011

Related U.S. Application Data

(62) Division of application No. 11/105,165, filed on Apr. 13, 2005, now Pat. No. 7,932,287.

(60) Provisional application No. 60/601,095, filed on Aug. 12, 2004.

(51) Int. Cl.
*A61K 31/195* (2006.01)

(52) U.S. Cl. ........................................ 514/561
(58) Field of Classification Search ................ 514/561
See application file for complete search history.

(56) References Cited

PUBLICATIONS

Rebouche et al., "Utilization of Dietary Precursors for Carnitine Synthesis in Human Adults", The Journal of Nutrition, vol. 119, No. 12, pp. 1907-1913 (1989).*

* cited by examiner

*Primary Examiner* — Kevin E Weddington
(74) *Attorney, Agent, or Firm* — Law Offices of Indu M. Anand; Indu M. Anand, Esq.

(57) ABSTRACT

The invention involves various embodiments of a method for treating a human being for a condition associated with (1) a clinical state of impairment of carnitine or carnitine esters, or decreased fatty acid metabolism, (2) low energy production or lower ATP production, (3) clinical hyperammonemia, and (4) clinically high pyruvate levels resulting from a deficiency in the biosynthesis of carnitine. The method involves administering a therapeutically effective salt of N-6-trimethyl-L-lysine.

2 Claims, No Drawings

METHOD OF TREATING A HUMAN BEING FOR A CLASS OF METABOLIC DEFECTS AND ENERGY PRODUCTION DISORDERS

CROSS-REFERENCE TO RELATED APPLICATIONS

This is a division of application Ser. No. 11/105,165, filed Apr. 13, 2005 now U.S. Pat. No. 7,932,287, which claims priority from provisional application No. 60/601,095 filed on Aug. 12, 2004, and incorporates the subject matter identified as Invention IV, VI, VII, and XIV in the Requirement for Restriction/Election of Jul. 25, 2008, in the parent application. All material referenced in the prior provisional and non-provisional applications are hereby incorporated by reference. This includes, but is not limited to, all specifications, drawings, and like materials.

Related divisional applications claiming similar priority include "Method of Synthesis and Purification of N-6-Trimethyl-L-Lysine and Derivative Compounds," "Derivative Compounds of N-6-Trimethyl-L-Lysine for Therapeutic Use," and "Method of Treating a Human Being for a Class of Neurological Defects and Seizure Disorders," Attorney Docket No. ChG_00114.

All books, manuals, articles, and papers that are cited herein are hereby incorporated by reference in their entirety.

BACKGROUND OF THE INVENTION

1. Field of Invention

This invention relates to treatment of human beings for conditions associated with deficiencies in the N-6-trimethyl-L-lysine (TML) pathway affecting biosynthesis of carnitine. Such conditions include (1) clinical hyperammonemia, (2) clinical state of impairment of carnitine or carnitine esters, (3) decreased fatty acid metabolism, (4) lower energy production or lower ATP production in the body, or (5) clinically high levels of pyruvate.

2. Description of Related Art

All material referenced in the prior provisional and non-provisional applications are hereby incorporated by reference.

Role of L-Carnitine

From a biochemical standpoint, L-carnitine plays an essential role in energy metabolism. In fatty acid metabolism, it serves as shuttle between the mitochondrial membrane and the mitochondria inner-workings permitting breakdown of the long-chain carbon fragment.

The more important role of L-carnitine is in maintaining a balance between the concentrations of a compound called acyl CoA in the cell compartments. For sugar to be metabolized, they are sequentially degraded to smaller fragments until carbon dioxide is produced, and along the way energy is conserved. Acyl CoA is an important intermediate in transfer of energy. Accordingly, it is important that the concentration of Acyl CoA be regulated and this function falls on L-carnitine. The role of L-carnitine and L-carnitine supplementation during exercise in humans has been illustrated (Brass E. P., Hiatt W. R., J. Am. Coll. Nutr., 17(3):207-215, 1998).

It has also been shown that defects in fatty acid oxidation are a source of major morbidity, particularly among children. Fatty acid oxidation defects encompass a spectrum of clinical disorders, including recurrent hypoglycemic, hypoketotic encephalopathy or Reye-like syndrome in infancy with secondary seizures and potential developmental delay, progressive lipid storage myopathy, recurrent myoglobinuria, neuropathy, and progressive cardiomyopathy. (I. Tein, J Child Neurol. 2002 December; 17 Suppl 3:3S57-82; discussion 3S82-3).

Supplementation or treatment of a number of these diseases/disorders with L-carnitine has had beneficial effects. For example, some researchers believe L-carnitine supplementation may complement other therapies for the treatment of AIDS. (Effect of L-carnitine on human immunodeficiency virus-1 infection-associated apoptosis; Moretti S., Alesse E., Di Marzio L., a pilot study. Blood, 91(10):3817-3824, 1998). According to the authors, the treatment of immunodeficiency virus type 1 infections, acquired immune deficiency syndrome (AIDS), may elicit or cause carnitine deficiency problems. Additionally, some epileptic patients may benefit from carnitine supplementation or treatment.

L-carnitine may be essential or "conditionally" essential for several groups of people including: normal infants, premature infants, and both children and adults suffering from a variety of genetic, infectious, and injury-related illnesses. For example, some cardiomyopathies, which afflict children, are due to metabolic errors or deficiencies. There is data that supports treatment of some myocardial dysfunctions with L-carnitine supplementation. (Winter, S., Jue, K., Prochazka J., Francis, P., Hamilton, W., Linn, L., Helton, E. (1995) J. Child Neurol. 10, Supple 2: S45-51.)

L-carnitine may also play an essential role in the treatment of several disease conditions. Administration of L-carnitine prevents acute ammonia toxicity and enhances the efficacy of ammonia elimination as urea and glutamine. In addition, the cytotoxic effects of ammonia, possibly arising from lipid peroxidation, are ameliorated by L-carnitine. These data indicate the feasibility of utilization of L-carnitine in the therapy of human hyperammonemic syndromes, both for reducing the levels of ammonia and preventing its toxic effects. (O'Connor J E, Adv Exp Med. Biol. 1990; 272:183-95).

L-carnitine deficiency can be defined as a decrease of intracellular L-carnitine, leading to an accumulation of acyl-CoA esters and an inhibition of acyl-transport via the mitochondrial inner membrane. This may cause disease by the following processes:

A. Inhibition of the mitochondrial oxidation of long-chain fatty acids during fasting causes heart or liver failure. The latter may cause encephalopathy by hypoketonaemia, hypoglycaemia and hyper-ammonaemia. It was shown that acetyl-L-carnitine fed to old rats partially restores mitochondrial function and ambulatory activity (Hagen T M, Ingersoll R. T, Wehr C. M, Proc. Natl. Acad. Sci. USA., 95(16): 9562-9566, 1998).

B. Increased acyl-CoA esters inhibit many enzymes and carriers. Long-chain acyl-CoA affects mitochondrial oxidative phosphorylation at the adenine nucleotide carrier, and also inhibits other mitochondrial enzymes such as glutamate dehydrogenase, L-carnitine acetyltransferase and NAD transhydrogenase. (Scholte H R, J Clin Chem Clin Biochem. May 1990; 28(5): 35)

C. Accumulation of triacylglycerols in organs increases stress susceptibility by an exaggerated response to hormonal stimuli (Iyer, R. N., Khan, A. A., Gupta, A., Vajifdar, B. U., Lokhandwala, Y. Y., J Assoc Physicians India, 8(11):1050-1052, 2000).

D. Effect of L-carnitine on exercise tolerance in chronic stable angina: a multicenter, double-blind, randomized, placebo controlled crossover study (Cherchi, A., Lai, C., Angelino, F., et al., Int. J. Clin. Pharmacol. Ther. Toxicol., 23(10): 569-572, 1985).

E. Decreased mitochondrial acetyl-export lowers acetylcholine synthesis in the nervous system.

Primary L-carnitine deficiency can be defined as a genetic defect in the transport or biosynthesis of L-carnitine. Until now, only defects at the level of L-carnitine transport have been discovered. The most severe form of primary L-carnitine deficiency is the consequence of a lesion of the L-carnitine transport protein in the brush border membrane of the renal tubules. This defect causes cardiomyopathy or hepatic encephalopathy usually in combination with skeletal myopathy. In a patient with cardiomyopathy and without myopathy, it was found that L-carnitine transport at the level of the small intestinal epithelial brush border was also inhibited. The patient was cured by L-carnitine supplementation. Muscle L-carnitine increased, but remained too low, suggesting that L-carnitine transport in muscle is also inhibited. L-carnitine transport in fibroblasts was normal, which disagrees with literature reports for similar patients. W. R. Treem, C. A. Stanley, D. N. Finegold, D. E. Hale, P. M. Coates, N. Engl. J. Med, 319, 1331-1336, 1988; G. Karpati, S. Carpenter, A. G. Engel, G. Watters, J., Allen, S. Rothman, G. Klassen, O. A. Mamer, Neurology, 25, 16-24, 1975; B. O. Eriksson, S. Lindstedt, I. Nordin, Eur. J. Pediatr., 147, 662-663, 1988; H. R. Scholte, R. Rodrigues Periera, P. C. de Jonge, I. E. Luyt-Houwen, M. Verduin, J. D. Ross, J. Clin. Chem. Clin. Biochem. 28, 351-357, 1990; C. A. Stanley, S. DeLeeuw, P. M. Coates, C. Vianey-Liaud, P. Divry, J. P. Bonnefont, J. M. Saudubray, M. Haymond, F. K. Tretz, G. N. Breningstall, Ann. Neuro. 30, 709-716, 1991; Y. Wang, J. Ye, V. Ganapati, N. Longo, Proc. Natl. Acad. Sci. USA 96, 2356-23601999.

In summary, L-carnitine plays a critical role in enhancing fat metabolism. Reports attest to the fact that L-carnitine works by transporting fatty acids to be burned for fuel, increasing both energy supply and lean muscle mass. Most reports also indicate that unless an individual is deficient in L-carnitine, it is an unnecessary ergogenic aid. This contrasts with an apparent need in case of L-carnitine deficiency (e.g., in the case pursued by the inventors of Late Infantile Neuronal Ceroid Lipofuscinosis—one form of Batten Disease), of the correct operation of the endogenous production of L-carnitine. This need was corroborated in the observations of dogs with Batten Disease given exogenous L-Carnitine (Siakotos A. N., Hutchins G. D., Farlow M. R., Katz M. L., European Journal of Paediatric Neurology 5 Suppl A: 151-6, 2001) and those of the parents of the child who was afflicted with LINCL (discussed below).

ATP Dependence on Endogenous L-Carnitine

Optimal ATP production from either dietary or stored fatty acids is dependent on L-carnitine. L-carnitine has several roles, most of which involve conjugation of acyl residues to the b-hydroxyl group of the L-carnitine with subsequent translocation of this complex from one cellular compartment to another. Deficiencies in L-carnitine have been implicated in a number of diseases. For example, in CLN3, proteins have been found to cause modulation of the cell growth rates and apoptosis (Persaud-Sawin D. A., Van Dongen A., Boustany R. M., Human Molecular Genetics. II (18):2129-42, 2002). It has been shown that defects in lysosomal enzymes cause Neuronal Ceroid Lipofuscinoses (NCLs), CLN1 and CLN2. (Hofmann S. L., Atashband A., Cho S. K., Das A. K., Gupta P., Lu J. Y., Current Molecular Medicine. 2(5):423-37, 2002). It has been also shown that the conditions of Parkinson's disease are present when there is dysfunction in both striatal and nigral neurons and this dysfunction results in autosomal dominant adult neuronal ceroid lipofuscinosis (Nijssen, P. C., Brusse, E., Leyten, A. C., Martin, J. J., Teepen, J. L., Roos, R. A., Movement Disorders, 17(3):482-7, 2002). It has been shown that abnormal accumulation of specific proteins occurs in the neuronal ceroid lipofuscinosis/Batten disease. These conditions result due to defect in the lysosomal proteases and related enzymes. The phenomenon is commonly termed as lysosomal proteinoses. This abnormal accumulation of proteins in the lysosomes has been shown to be responsible for major diseases such as Alzheimer disease, alpha-synuclein in Parkinson's disease, Lewy body dementia (Gupta, P., Hofmann, S. L., Molecular Psychiatry. 7(5):434-6, 2002). An autoantibody inhibitory to glutamic acid decarboxylase in the neurodegenerative disorder, Batten disease has been reported (Chattopadhyay, S., Ito, M., Cooper, J. D., Brooks, A. I., Curran, T. M., Powers, J. M., Pearce, D. A., Human Molecular Genetics. 11(12): 1421-31, 2002). Mutations in different proteins result in similar diseases of neuronal ceroid lipofuscinoses (Weimer, J. M., Kriscenski-Perry, E., Elshatory, Y., Pearce, D. A., NeuroMolecular Medicine. 1(2): 111-24, 2002). Lysosomal localization of the neuronal ceroid lipofuscinosis CLN5 protein. (Isosomppi, J., Vesa, J., Jalanko, A., Peltonen, L., Human Molecular Genetics. 11(8): 885-91, 2002).

Carnitine Biosynthesis & Metabolism

N-6-Trimethyl-L-Lysine (TML)

The enzyme Tripeptidyl Peptidase 1 (TPP-1) is responsible for cleaving "protein bound N-6-trimethyl-L-lysine" with the resulting products of free TML and amino acids in normal people. However, in children who have Late-Infantile Neuronal Ceroid Lipofuscinoses (LINCL), the TPP-1 is defective and the "protein-bound TML" is not broken down (M. L. Kaz, Biochem. Biophy. Acta, 1317, 192-198, 1996). It therefore becomes the storage material in the lysosome. Eventually it builds up and then consequently "blows up" the lysosome, causing eventual massive neuronal damage in brain and eventually death (P. Gupta and S. L. Hofmann, Molecular Psychiatry, 7, 434-436, 2002).

It has been shown that there is specific accumulation of a hydrophobic protein, subunit c of ATP synthase, in lysosomes from the cells of patients with LINCL, and is caused by a defect in the CLN2 gene product, TPP-1. The data by the authors show that TPP-1 is involved in the initial degradation of subunit c in lysosomes and suggest that its absence leads directly to the lysosomal accumulation of subunit c (Ezaki, J., Takeda-Ezaki, M., Kominami, E., J Biochem (tokyo) September, 128(3), 509, 2000).

Lysosomal hydrolysis of these proteins results in the release of TML, which is the first metabolite of L-carnitine biosynthesis. Hepatic synthesis of carnitine takes place from protein-bound N-6-trimethyl-L-lysine. Lysosmal digestion of methyl-lysine labeled asialo-fetuin was carried out (LaBadie, J., Dunn, W. A. and Aronson Jr, N. N. Biochem. J. 160, 85-95, 1976). L-carnitine biosynthesis has been studied, such as, from gamma-butyrobetaine and from exogenous protein-bound-6-N-trimethyl-L-lysine by perfused guinea pig liver. In this connection, the effect of ascorbate deficiency on the in situ activity of gamma-butyrobetaine hydroxylase was demonstrated (Dunn, W. A., Rettura, G., Seifter, E. and Englard, S., J. Biol. Chem. 259, 10764-10770, 1984).

TML to L-Carnitine Pathway

TML is first hydroxylated on its 3-position to form 3-hydroxy-N-6-trimethyl-L-lysine (HTML). The aldolytic cleavage of HTML with HTML Aldolase (HTMLA) yields trimethylaminobutyraldehyde (TMABA) and glycine. Dehydrogenation of TMABA by TMABA dehydrogenase (TMABA-DH) results in the formation of 4-N-trimethylaminobutyrate (butyrobetaine). In the last step, gamma-butyrobetaine is hydroxylated on the 3 position by gamma-butyrobetain deoxygenase (BBD; EC to yield L-carnitine (Frederic M. Vaz and Ronald J. A. Wanders, Biochem. J. 361, 417-429, 2000). Very little is known about HTMLA. It might be identical to serine and lycine hydroxymethyltransferase (SHMT) which catalyses the tetrahydrofolate-dependent interconversion of serine and glycine (Girgis, S., Nasrallah, I. M., Suh, J. R., Oppenheim, E., Zanetti, K. A., Mastri, M. G. and Stover, P. J., Gene 210, 315-324, 1998). Purification and characterization of cytosolic and mitochondrial serine hydroxymethyltrasferase from rat liver was carried out (Ogawa, H. and Fujioka, M. J. Biochem. (Tokyo) 90, 381-390, 1981). SHMT also catalyses the aldol cleavage of other beta-hydroxylamino acids in absence of tetrahydrofolate, including HTML (Girgis, S., Nasrallah, I. M., Suh, J. R., Oppenheim, E., Zanetti, K. A., Mastri, M. G. and Stover, P. J. Gene 210, 315-324, 1998). Synthesis of butyrobetaine and L-carnitine from protein bound TML is inhibited by 1-amino-D-proline, an antagonist of vitamin B6. This inhibitory effect of 1-amino-D-proline on the production of L-carnitine from exogenous protein-bound N-6-trimethyl-L-lysine by the perfused rat liver has been shown. (Dunn, W. A., Aronson Jr, N. N. and Englard, S., J. Biol. Chem. 257, 7948-7951, 1982).

It is well known from the biochemistry of the metabolic pathway of TML to HTML that certain cofactors; such as 2-oxoglutarate, $Fe^{2+}$, molecular oxygen and ascorbate, have to be present. Similarly in the subsequent steps of metabolic pathway from HTML to L-carnitine, the biochemically defined cofactors have to be present. The cofactors (2-oxoglutarate, $Fe^{2+}$, molecular oxygen, and ascorbate) have been established by a number of researchers during the enzymatic hydroxylation of TML. It is likely that other chemicals will work as cofactors as well. For example, DTT (dithiothreitol) has been used instead of ascorbic acid (which is required to keep $Fe^{2+}$ in reduced form), in test tube conditions. Besides the aforesaid cofactors, calcium ion was found to cause significant enhancement in the conversion of TML to HTML (D. S. Sachan, C. L. Hoppel, Biochem. J., 188, 529-534, 1980).

4-N-trimethylaminobutyraldehyde dehydrogenase (TMABA-DH) catalyzes the dehydrogenation of 4-N-trimethylamino butyraldehyde to butyrobetaine. TMABA-DH has an absolute requirement for $NAD^+$. In human tissues, the rate of TMABA dehydrogenation is highest in liver, substantial in kidney, but low in brain, heart and muscle (Rebouche, C. J. and Engel, A. G., Biochim. Biophys. Acta, 22-29, 1980). TMABA-DH has been purified from beef liver (Hulse, J. D. and Henderson, L. M., Fed. Proc. Fed. Am. Soc. Exp. Biol., 38, 676, 1979).

Gamma-butyrobetaine dioxygenase (BBD) catalyses the stereospecific hydroxylation of butyrobetaine to L-carnitine in mammalian studies. BBD activity was stimulated considerably by 2-oxoglutarate, and the enzyme requires molecular oxygen, $Fe^{2+}$ and ascorbate for activity. (Lindblad, B., Lindstedt, G. and Tofft, M., J. Am. Chem. Soc., 91, 4604-4606, 1969). BBD activity has been found to be localized in the cytosol.

Kakimoto and Akazawa were the first to identify TML in human urine. All methods to assay TML in either plasma, urine or tissue samples use the same sample work-up. The concentration of TML in plasma is relatively constant in both human and rat, ranging from 0.2 to 1.3 micromole. Plasma levels of TML have been shown to correlate with body mass. In humans, urinary TML concentration is proportional to that of creatine. Furthermore, TML is not reabsorbed by kidney in humans. (Davis, A. T., Ingalls, S. T. and Hoppel, C. L J. Chromatogr. 306, 79-87, 1984.). In humans, TML concentrations range between 2 to 8 micromole per mmole of creatine. (Kakimoto, Y. and Akazawa, S., J. Biol. Chem. 245, 5751-5758, 1970).

Butyrobetaine is the last step in the synthesis of L-carnitine. The level of butyrobetaine in urine is low (about 0.3 micromole/mmol creatinine) (F. M. Vaz, B. Melegh, J. Bene, D. Cuebas, D. A. Gage, A Bootsma, P. Vreken, A. H. van Gennip, L. L. Bieber and R. J. A. Wanders, unpublished work) compared with the concentration in plasma of 4.8 micromole (Sandor, A., Minkler, P. E., Ingalls, S. T. and Hoppel, C. L., Clin. Chim. Acta., 176, 17-27, 1988).

Factors in the Biosynthesis & Control of L-Carnitine and N-6-Trimethyl-L-Lysine

Major sources of L-carnitine in the human diet are meat, fish and dairy products. Omnivorous humans generally ingest 2-12 micromoles of L-carnitine per day per kg of body weight. This is more than the L-carnitine produced endogenously, which has been estimated to be 1.2 micromole per day per kg of body weight. In omnivorous humans, approximately 75% of body L-carnitine sources come from the diet and 25% come from de novo biosynthesis. Since L-carnitine is present primarily in foods of animal origin, strict vegetarians obtain <0.1 micromole per day per kg of body weight. Strict vegetarians obtain more than 90% of their L-carnitine through biosynthesis.

Two primary intermediates have been proposed as the factors which limit biosynthesis of L-carnitine via their availability. These two intermediaries are g-butyrobetaine and N-6-trimethyl-L-lysine. Studies have shown that increasing the amount of either of these two intermediates in the bloodstream will increase the production of L-carnitine 100-fold in rats and 3-fold in human infants and adults (Olson and Rebouche, J. Nutr. 117(6), 1024-31, 1987). Thus, L-carnitine biosynthesis may be regulated by one or all of the three enzymes which, together, catalyze the transformation of N-6-trimethyl-L-lysine into g-butyrobetaine. The high level of L-carnitine synthesis from exogenous L-carnitine precursors suggests that the enzymatic capacity to synthesize L-carnitine from TML and butyrobetain is much higher than is usually utilized. This suggests that only the availability of TML is the rate limiting step in the regulation of feedback inhibition for L-carnitine biosynthesis (Schematic 1). (F. M. Vaz and R. J. A. Wandars, Biochem. J., 361, 417-429, 2002).

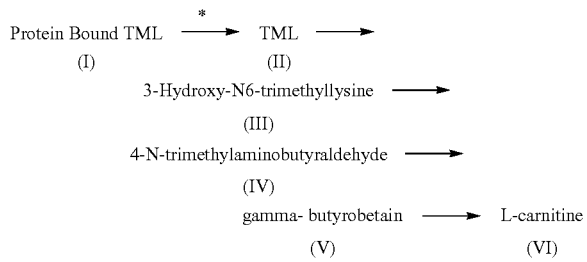

Schematic 1 -
Biosynthesis of L-Carnitine from TML (feedback regulation of TML)

Protein Bound TML ⟶* TML ⟶
(I) (II)
3-Hydroxy-N6-trimethyllysine ⟶
(III)
4-N-trimethylaminobutyraldehyde ⟶
(IV)
gamma- butyrobetain ⟶ L-carnitine
(V) (VI)

*(rate limiting step for L-carnitine biosynthesis and feedback inhibition of L-carnitine)

L-ascorbic acid may be a principle co-factor in the metabolism of L-carnitine. It has been postulated and demonstrated that an experimental vitamin C deficiency resulted in increased urinary excretion of L-carnitine. This increased excretion of L-carnitine may be due to either decreased absorption from dietary sources, or increased excretion from the kidney. Several methods have been described to measure the concentration of L-carnitine biosynthesis metabolites in biological fluids and tissues.

The kidney plays a major role in L-carnitine biosynthesis, excretion and acylation. Unlike in the rat, human kidney contains the enzymes needed to form L-carnitine from N-6 trimethyl-L-lysine (K, Doqi, National Kidney Foundation. Am. J. Kidney Dis., 35, 6 Suppl 2 S1-140, 2000). This L-carnitine precursor, TML, is found to be increased in plasma of patients with chronic renal failure. Free L-carnitine formed in the kidney as well as L-carnitine reabsorbed from the glomerular filtrate may be acylated in the proximal tubule. Isolated rat cortical tubule suspensions contain total L-carnitine concentrations of 2.85 micromols/g protein. During incubation over 60 min, the acylcarnitine/carnitine ratio decreased, indicating deacylation of acylcarnitine in proximal tubules. Exogenous L-carnitine was acylated at a rate of 35 micromols/h/g protein. Besides pyruvate and acetate, ketone bodies stimulated the acylation rate several fold, indicating that these substrates are a major source of acetyl-CoA for the acylation reaction. This may explain the higher acetylcarnitine/L-carnitine ratio found in urine under ketotic conditions.

However, later data shows that the brain participates in active synthesis of L-carnitine from TML takes place (F. M. Vaz and R. J. A. Wandars, Biochem. J., 361, 417-429, 2002). The concentration of butyrobetaine in plasma and tissues was determined by isolating butyrobetaine via HPLC or ion-exchange chromatography, and using BBD to convert it into L-carnitine. In humans, the level of butyrobetaine in urine is low (about 0.3 micromole/mmole L-creatinine) compared with the concentrations in plasma (4.8 mmole & 1.8 mmole).

The concentration of L-carnitine in plasma from both humans and rats is age and sex dependent. In humans, the plasma L-carnitine concentration increases during first year of life (from about 0.15 to about 0.40 mmole) and remains the same for both sexes until puberty. From puberty to adulthood, plasma L-carnitine concentrations in males increases and stabilizes at a level that is significantly higher than those in females (50 micromole compared to 40 micromole).

Obviously, carnitine is available from exogenous sources (meat, milk). However, work has been done to see if exogenous carnitine would ameliorate the symptoms of Juvenile Neuronal Ceroid Lipofuscinosis, not LINCL. This research in dogs showed that it made the dogs more functional and they lived 10% longer than untreated dogs, but the dogs still died very young compared to unaffected dogs and brain glucose hypometabolism and cerebral atrophy were not reduced (Siakotis, Katz et al., European Journal Pediatric Neurology 5, (Suppl. A): 151-156, 2001). It is an exciting prospect to see that TML may indeed be that therapeutic agent to cause positive brain metabolism based upon the results we have seen.

This invention provides a method of exogenic supplementation with TML to affect L-carnitine biosynthesis, thereby influencing ATP levels.

SUMMARY OF THE INVENTION

The present invention provides a method of administering a pharmaceutically acceptable salt of said N-6-trimethyl-L-lysine (TML) or TML derivative for treatment of conditions associated with a deficiency in the N-6-trimethyl-L-lysine pathway affecting biosynthesis of carnitine.

The modified TML derivatives described should have similar or near-similar results and improved biochemical properties. One of ordinary skill in the art would recognize that structural derivatives of TML, such as those mentioned in this application, may participate in the same biological processes and have the same and improved biochemical properties.

In one embodiment, the invention includes formulations or encapsulations of the compounds shown in Formulas I-VI for efficient intracellular delivery and as a prodrug of TML to proceed to make endogenous L-carnitine, and to participate in various metabolic activities in the intermediate steps of L-carnitine biosynthesis pathway. These may be used for better adsorption of modified TML into various tissues such as kidney, liver and brain. The R', R", and aminoacyl groups are expected to hydrolyze inside the cellular media with one or more intracellular esterases to release free TML. Intracellular esterases are known to hydrolyze esters (Ghosh, M. and Mitra, A. K., Effects of 5'-Ester Modification on the Physicochemical Properties and Plasma Protein Binding of 5-Iodo-2'-Deoxyuridine. Pharm. Res., 8, 771-775, 1991).

It is believed these can be used to treat a human being diagnosed with one or more of the following: defects in carnitine biosynthesis pathway, efficiency of endogeneous TML, over-accumulation of TML bound protein at the cellular level, hyperammonemic encephalopathy, over-accumulation of glutamine in the brain, reduced and deficient fatty acid metabolism and shuttling of fatty acid in to mitochondria, insufficient ATP production or subsequent energy production and all the cellular activities associated with this events, defective fatty acid oxidation resulting from carnitine deficiency, hypoglycemia, hypoketotic encephalopathy, reye-like syndrome, ammonia over-production, hyperammonemic syndromes, over accumulation of triacylglycrols, and lysosomal accumulation of mitochondrial ATP synthase subunit and their by products.

The invention utilizes compounds represented by Formulas I-VI, and having at least 98% purity; and preparations, prodrugs, formulations, and encapsulated forms thereof. The CAS number for the TML compound is 23284-33-5.

The chemical structure of TML is commonly known to one of ordinary skill and the art and is represented by Formula I below:

Formula I

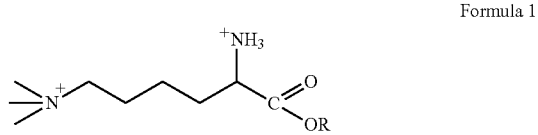

The TML derivatives are represented by the following Formulas II-VI:

Formula II:

Formula II

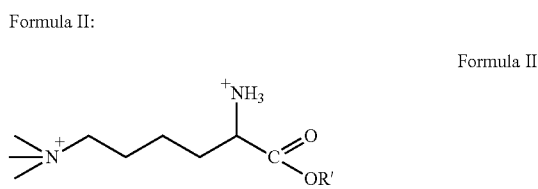

wherein R' is selected from the group consisting of an alkyl having between 1 and 5 carbon atoms and an aromatic ring.

Formula III:

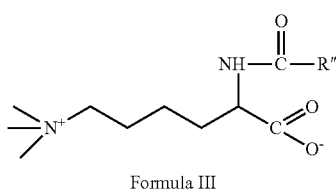

Formula III wherein R″ is an alkyl having 1 to 5 carbon atoms or CH3.

Formula IV:

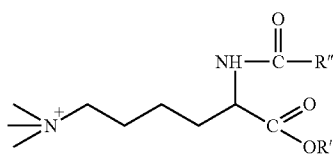

Formula IV wherein R″ is an alkyl having between 1 and 5 carbon atoms, or CH3 and R' is an alkyl having between 1 and 5 carbon atoms or an aromatic ring.

Formula V:

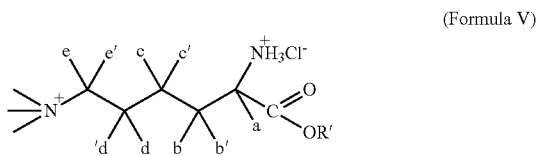

(Formula V)

wherein a, a', b, b'; c, c', d, d', e, and e' are independently selected from H, deuterium, and an alkyl having between 1 and 5 carbon atoms; R' is selected from the group consisting of H, an alkyl having between 1 and 5 carbon atoms and an aromatic ring; and, and each N is independently selected from nitrogen and N15 labeled nitrogen.

Formula VI:

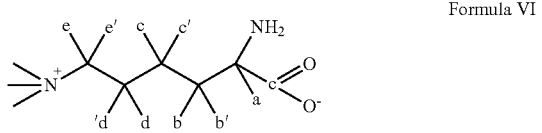

Formula VI wherein the a, b, b', c, c', d, d', e, and e' are independently selected from H, deuterium, and an alkyl having from 1 to 5 carbon atoms, and each N is independently selected from nitrogen and N15 labeled nitrogen.

DETAILED DESCRIPTION OF THE INVENTION

As used herein, the term "derivative" means any of Formulas II-VI. The invention incorporates both TML and TML derivatives. As such, any mention of TML also encapsulates the TML derivative compounds.

The phrase "pharmaceutically acceptable" indicates that the designated carrier, vehicle, diluent, excipient(s), and/or salt must be chemically and/or physically compatible with the other ingredients comprising the formulation, and physiologically compatible with the recipient thereof.

The term "prodrug" refers to a compound that is a drug or supplement precursor which, following administration, releases the drug or supplement in vivo via a chemical or physiological process (e.g., upon being brought to physiological pH or through enzyme activity). A discussion of the synthesis and use of prodrugs is provided by T. Higuchi and W. Stella, "Prodrugs as Novel Delivery Systems, Vol. 14 of the ACS Symposium Series, and in Bioreverible Carriers in Drug Design, ed. Edward B. Roche, American Pharmaceutical Association and Pergamon Press, 1987.

The term "treat" means to ameliorate or prevent at least one symptom of a disease or a condition.

As used herein, a "salt" can be an internal salt or an external salt. In internal salt, the carboxylic group (which is negatively charged) and the trimethyl group (which is positively charged) form an internal salt. The alpha amino group picks up the proton from the ionized carboxylic group when there is no external salt. In other embodiments, the proton from the ionized carboxylic group is picked up by one or more counterions (i.e., external molecule, atom, or group of atoms) thus forming the external salt. Sometimes, the counter ions can aggregate to include multiple ions. A typical example will be a molecule of water. These are generally multiple molecules and not a single molecule of water attached to a single ion.

Usually, the compound will include one or more different counterions (usually one for each of the two cationic sites in the molecules). The counter ions could be HO⁻, halides, sulfhydryl, carboxylic, phosphines, amines, organic anions, inorganic anions, or a mixture of organic and inorganic anions. These are well known to the skilled artisan. In some cases, there may only be one type of counter ion since internal zwitterions could leave only a single cationic site for salt formation.

One of ordinary skill in the art will further understand that the TML compound, Formula 1, is charged and thus has an internal salt or an external salt. External salts require one or more counterions. Hence, this compound may also include different counterions (usually one for each of the two cationic sites in the molecules). The counter ions could be HO⁻, halides, sulfhydryl, carboxylic, phosphines, amines, organic anions, inorganic anions, or a mixture of organic and inorganic anions, or other well known counterions In some cases, there may only be one type of counterion since internal zwitterions could leave only a single cationic site for salt formation. In yet another embodiment, there may be no counterions because there is an internal salt.

In another embodiment, the invention includes formulations or encapsulations of TML for efficient intracellular delivery and as a prodrug of TML to proceed to make endogeneous L-carnitine, and to participate in various metabolic activities in the intermediate steps of L-carnitine biosynthesis pathway. These may be used for better adsorption of modified TML into various tissues such as kidney, liver and brain.

TML is further provided in a physiologically acceptable carrier. These include various solvents, dispersion media, coatings, antibacterial and antifungal agents, isotonic and absorption delaying agents and like. The use of such media and agents for pharmaceutically active substances is well known in the art. Except, in so far as any conventional media or agent is incompatible with the active ingredient, its use in the therapeutic and supplement compositions is contemplated. Supplementary active ingredients can also be incorporated into the compositions.

These pharmaceutical and supplement formulations can be used to treat the afflicted diseases or disorders and conditions resulting from the TML deficiency and imbalance in the endogeneous L-carnitine biosynthesis pathway.

The method is to be in amount sufficient to exert the biochemical response and increase the conditions towards normalization.

The effective dosage of TML (or the pharmaceutically acceptable salt) and mode of administration in the treatment or improvement of conditions of various disorders can be determined by routine experimentation. The pharmaceutical or supplementation forms suitable for injectable use, or oral use, include sterile aqueous solutions or dispersions and sterile powders for the extemporaneous preparation of sterile injectable solutions or dispersions or oral formulations. In all cases the form must be sterile. It must be stable under the conditions of manufacture and storage and may be prepared against the contaminating effects and actions of microorganisms, such as bacterial and fungi. The carrier can be solvent or dispersion medium. The prevention of the action of microorganisms can be brought about by various antibacterial and antifungal agents. Prolonged absorption of the injectable or oral form can be brought about by the use of the compositions of agents delaying absorption.

TML (or the pharmaceutically acceptable salt) may be administered by any useful route including intravenous, intraperitoneal injection, intranasal, rectal, oral, transdermal or subcutaneous administration. Sterile injectable solutions are prepared by incorporating TML (or the pharmaceutically acceptable salt) in the required amount in the appropriate solvent, followed by sterilization.

TML (or the pharmaceutically acceptable salt) may be administered to a human being at dosage levels in the range of from about 0.1 mg to about 3,000 mg per day. For example, for a normal adult human having a body mass of about 70 kg, a dosage in the range of from about 0.01 mg to about 100 mg per kg body mass is typically sufficient. However, some variability in the general dosage range may be required depending upon the age and mass of the subject being treated, the intended route of administration, the particular compound being administered, and the like. The determination of dosage ranges and optimal dosages for a particular human subject is within the ability of one of ordinary skill in the art having benefit of the instant disclosure.

The pharmaceutical compositions of the invention may further comprise adjuvants, such as preserving, wetting, emulsifying, and dispersing agents. Prevention of microorganism contamination of the instant compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions may be affected by the use of agents capable of delaying absorption, for example, aluminum monostearate and gelatin.

Solid dosage forms for oral administration include capsules, tablets, powders, and granules. In such solid dosage forms, the active compound is admixed with at least one inert conventional pharmaceutical excipient (or carrier) such as sodium citrate or dicalcium phosphate, or (a) fillers or extenders, as for example, starches, lactose, sucrose, mannitol, and silicic acid; (b) binders, as for example, carboxymethylcellulose, alginates, gelatin, polyvinylpyrrolidone, sucrose, and acacia; (c) humectants, as for example, glycerol; (d) disintegrating agents, as for example, agar-agar, calcium carbonate, potato or tapioca starch, alginic acid certain complex silicates, and sodium carbonate; (e) solution retarders, as for example, paraffin; (f) absorption accelerators, as for example, quaternary ammonium compounds; (g) wetting agents, as for example, acetyl alcohol and glycerol monostearate; (h) adsorbents, as for example, kaolin and bentonite; and/or (i) lubricants, as for example, talc, calcium stearate, magnesium stearate, solid polyethylene glycols, sodium lauryl sulfate, or mixtures thereof. In the case of capsules and tablets, the dosage forms may further comprise buffering agents.

Solid compositions of a similar type may also be employed as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well-known to one of ordinary skill in the art. They may also comprise opacifying agents, and can also be of such composition that they release the active compound in a delayed, sustained, or controlled manner. Examples of embedding compositions that can be employed are polymeric substances and waxes. The active compound can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil, and sesame seed oil, glycerol, tetrahydrofurfuryl alcohol, polyethylene glycols and fatty acid esters of sorbitan, or mixtures of these substances, and the like.

Besides such inert diluents, the pharmaceutical composition can also include adjuvants, such as wetting agents, emulsifying and suspending agents, sweetening, flavoring, and perfuming agents.

Suspensions, in addition to the active compound, may further comprise suspending agents, as for example, ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing an active compound with suitable non-irritating excipients or carriers such as cocoa butter, polyethylene glycol or a suppository wax, which are solid at ordinary room temperature, but liquid at body temperature, and therefore, melt in the rectum or vaginal cavity thereby releasing the active component.

Dosage forms for topical administration may comprise ointments, powders, sprays and inhalants. The active agent are admixed under sterile condition with a pharmaceutically acceptable carrier, vehicle, or diluent, and any preservatives, buffers, or propellants that may be required.

In one embodiment of the invention, the compounds of Formula I is administered to a human being along with supplementation for one or more co-factors required for carnitine biosynthesis. It is believed that the necessary co-factors are generally ingested through a normal diet or synthesized in vivo.

In another embodiment of the invention, any of the compounds of Formula I is administered to a human being along with supplementation for one or more co-factors required for the hydroxylation of N6-trimethyl-L-lysine by TML dioxygenase. These co-factors are: 2-oxoglutarate (alpha keto glutarate), Fe2+, and ascorbate. Substitutes have also been found to be effective. For example, reducing agents such as dithiothreitol can take the place of ascorbate. (Vaz and Wanders, Biochem J. (2002) 361, 417-429). Molecular oxygen is also a co-factor, but is not required since a human being would breathe it in. Preferably, the one or more co-factors is given to the human being in an amount that is in excess of the molar equivalent of the TML or TML derivative administered to the human being. Calcium ion was found to cause significant enhancement in the conversion of TML to HTML (D. S. Sachan, C. L. Hoppel, Biochem. J., 188, 529-534, 1980). Thus, in a preferred embodiment, calcium ion supplementation is further administered to the human being, most preferably in an amount that is in excess of the molar equivalent of the given TML.

Experimental Study: Delivery of TML to a Child Diagnosed with Late Infantile Neuronal Ceroid Lipofuscinosis (LINCL) (Patient; Female, Age 6. Weight; 27 lbs, Length: 36 Inches)

Child had been taking the supplements/vitamins listed in Appendix B for about three years before the start of TML therapy. In addition, she had been taking clonazepam (5-(2-chlorophenyl)-1,3-dihydro-7-nitro-2H-1,4-benzodiazepin-2-one) which is sold under the trade name Klonopin by F. Hoffmann-La Roche Ltd. (Basel, Switzerland) for control of constant Myoclonic seizures for about the same time according to the following daily dosage: (a) at waking: ½ of one 0.5 mg tablet, (b) Every four hours after waking, ¼ of one 0.5 mg tablet, (c) At bedtime: ½ of one 0.5 mg tablet. She also took one (1) 25 mg capsule of nitrofurantoin macrocrystals (sold under the name Macrodantin by Procter & Gamble Pharmaceuticals, Cincinnati Ohio) once per day.

"Baseline" blood work was done after an overnight fast on the morning of Nov. 19, 2003. Child received her usual supplements/vitamins, clonazepam, and macrodantin. TML, as synthesized in Example 1 was given to the patient (5 mg of TML per day for a 30 day period, ending Dec. 28, 2003). Between Dec. 28, 2003 and Jan. 24, 2004, the child was given an alternating daily dose of 5 mg/day and 10 mg/day. On Jan. 24, 2004, and till the "new" blood work was done on Jan. 29, 2004, the patient received 10 mg/day by usually taking 5 mg of TML with breakfast and 5 mg of TML with dinner. She received 5 mg per dose during the duration of the experiment. In other words, she received TML once per day on days that she received 5 mg, and TML twice per day on days that she received 10 mg of TML. The TML was administered in powder form intermixed with her food.

Result after TML Therapy

The child's blood work results are in Table A, below, and the empirical nature of the child's improvement is evidenced by the follow up blood results. These blood tests were standard clinical tests carried out at Children's Hospital of Pittsburgh.

TABLE A

Results After TML Therapy.

| Test Name | Nov. 19, 2003 | Clinical Range | Jan. 29, 2004 | Clinical Range |
|---|---|---|---|---|
| Hgb | 14.4 | high | 14 | normal |
| HCT | 42 | high | 40.3 | normal |
| RDW | 11.5 | high | 12.3 | normal |
| ABS Lymphocytes | 2.2 | low | 2.5 | normal |
| Glycine | 50 | high | 25 | normal |
| Taurine | 24 | high | 19 | normal |

TABLE A-continued

Results After TML Therapy.

| Test Name | Nov. 19, 2003 | Clinical Range | Jan. 29, 2004 | Clinical Range |
|---|---|---|---|---|
| Carnitine, Total | 40 | normal | 43 | normal |
| Carnitine, Esters | 7 | normal | 10 | normal |
| Alanine | 87 | high | 47 | normal |
| Carbon Dioxide | 32 | high | 22 | normal |
| BUN | 2 | low | 5 | (low) (6 is norm!) |
| AST | 60 | high | 50 (high) | (40 is norm) |
| Platelets | 586 | high | 461 (high) | (369 norm) |
| Glutamine | 99 | high | 70 | normal |

Notes to the Table A:
(a) HCB = hemoglobin, HCT = Hematocrit, RDW Red Cell Distribution Width, ABS absolute, BUN Blood Urea Nitrogen, AST = Aspartate Amonotransferase)
(b) The examining physicians comments of Nov. 19, 2003 regarding Table A: (I) Alanine is elevated, this may be seen in states with increased pyruvate, (ii) Glutamine is increased, this may be seen, with Hyperammonemia. The clinical correlation is indicated.
(c) The examining physicians comments on Jan. 29, 2004 that no significant elevation of serum amino acid was seen.
(d) The patient's glucose and potassium increased (Glucose 93 baseline to 132; Potassium 4.4 baseline to 4.8). Even though the follow up blood work was done after an all night fast, we did give her some "Gatorade" to drink before the blood test. This was given with her Klonopin to wash it down and certainly could be a contributing factor to the rise in glucose and potassium.

After Jan. 29, 2004, her parents continued giving her TML in varying doses (5 mg-30 mg) per day. The varying doses were based on the family's attempt to find an optimal dose. Her condition remained stable through January 2005.

Discussion of Experimental Study Results

Carnitine and Carnitine Esters

In the correspondence (remarks) from the inventors received by the USPTO on Oct. 27, 2008 (mail room date), the inventors indicated that with the TML supplementation and treatment, the carnitine esters increased by 42.86% from Nov. 19, 2003 to Jan. 29, 2004, as measured by the blood levels in the subject patient, even though during the same period the carnitine level increased by 7.5%.

The significance of this data lies in the following observation: We have the ability to directly influence the carnitine esters, and consequently biological availability of carnitine, with the exogenous TML-based therapeutic intervention.

In Chalmers et al. (Urinary Excretion of 1-Carnitine and Acylcarnitines by Patients with Disorders of Organic Acid Metabolism: Evidence for Secondary Insufficiency of 1-Carnitine, PEDIATRIC RESEARCH, pp 1325-1328, Vol. 18, No. 12, 1984) the authors claim that additional newly proposed roles for carnitine recognize the ability of carnitine to act as a cofactor in the transfer of acyl groups out of the mitochondrion, in the reverse direction to the classical role. In particular, the acetyl moiety of acetyl-CoA produced within the mitochondria may be transferred in this manner under certain conditions to the cytoplasm. Chalmers et al., at 1328.

The fact that the carnitine esters were higher in the follow-up bloodwork (10 on Jan. 29, 2004 versus 7 on Nov. 19, 2003) are proof of the fact that by supplementing the patient with oral TML stimulated the N-6-trimethyl-L-lysine (TML) pathway affecting biosynthesis of carnitine (Carnitine Biosynthesis Pathway) producing endogenous carnitine in the mitochondrial matrix, providing the opportunity for this newly produced endogenous carnitine to bind with the 'acyl' groups and transport them out of the mitochondria. This ultimately is reflected in the higher level of Carnitine esters (10 on Jan. 29, 2004 versus 7 on Nov. 19, 2003). It is only through stimulating the production of endogenous carnitine (in this case via the supplementation of exogenous TML to stimulate the Carnitine Biosynthesis Pathway) do the wheels of metabolism turn.

Long-chain acylcarnitines cross the inner mitochondrial membrane in exchange for free carnitine via a specific translocase. In the matrix space acylcarnitines become substrate for carnitine acyltransferase II for reformation of acyl-CoAs, which are substrates for B-oxidation. During this reaction carnitine is regenerated. The end product of an undisturbed B-oxidation is acetyl-CoA, which has four major routes of disposal: ketogenesis, oxidation by the Krebs cycle, hydrolysis to acetate and conversion to acteylcarnitine. The article goes on to state that the intramitochondrial relationship between acyl-CoA and free CoA is reflected by the extramitochondrial acylcarnitine to free carnitine ratio (acyl-CoA/CoA=acylcarnitine/carnitine; AC/FC). The diagnostic value of the acylcarnitine determination can only be appreciated if it is realized that any mitochondrial acyl-CoA accumulation leads to a corresponding increase in acyl-carnitines. Acylcarnitines in blood and urine therefore reflect the accumulation of acyl-CoA esters in the mitochondrial matrix. Carnitine Esters in Metabolic Disease, Böhles et al. Eur J Pediatr (1994) 153 [Suppl 1]:S57-S61.

$$\frac{\text{Total AcylCarnitine}}{\text{Total Carnitine}} = \text{Carnitine Ratio}$$

In our patient, the 'baseline' bloodwork on Nov. 19, 2003 regarding the 'Carnitine Ratio' looked like this:

$$\frac{\text{Total AcylCarnitine}}{\text{Total Carnitine}} = \text{Carnitine Ratio or } \frac{7}{40} = 0.175$$

In our patient the 'follow up' bloodwork on Jan. 29, 2004 looked like this:

$$\frac{\text{Total AcylCarnitine}}{\text{Total Carnitine}} = \text{Carnitine Ratio or } \frac{10}{43} = 0.2326$$

As previously stated, the exogenous TML supplementation on the patient produced a 42.86% increase in Carnitine esters (AcylCarnitine) and a 7.5% increase Carnitine in the follow up bloodwork. The 'Carnitine Ratio' went from being low at 0.175 to Normal at 0.2326. Under normal conditions about 80% of serum carnitine is free carnitine, with a normal AC/FC ratio of 0.25, ACFC ratios>0.40 are considered abnormal (Carnitine Esters in Metabolic Disease, Böhles et al. Eur J Pediatr (1994) 153 [Suppl 1]:S57-S61).

In light of the many symptoms that were ameliorated in the patient supplemented with exogenous TML, we consider this to be of very significant impact because in the Chalmers et al. the authors state in the abstract that concentrations of 1-carnitine and acylcarnitines have been determined in urine from patients with disorders of organic acid metabolism associated with an intramitochondrial accumulation of acyl-CoA intermediates. These included propionic acidemia, methylmalonic aciduria, isovaleric acidemia, multicarboxylase deficiency, 3-hydroxy-3-methylglutaric aciduria, methylacetoacetyl-CoA thiolase deficiency, and various dicarboxylic acidurias including glutaric aciduria, medium-chain acyl-CoA dehydrogenase deficiency, and multiple acyl-CoA dehydrogenase deficiency. In all cases, concentrations of acylcarnitines were greatly increased above normal with free carnitine concentrations ranging from undetectable to supranormal values. The ratios of acylcarnitine/carnitine were elevated above the normal value of 2.0+/−1.1. 1-Carnitine was given to three of these patients; in each case, concentrations of plasma and urine carnitines increased accompanied by a marked increase in concentrations of short-chain acylcarnitines.

Despite naturally occurring attempts to increase endogenous 1-carnitine biosynthesis, there is insufficient carnitine available to restore the mass action ratio as demonstrated by the further increase in acylcarnitine excretion when patients were given oral 1-carnitine (Urinary Excretion of 1-Carnitine and Acylcarnitines by Patients with Disorders of Organic Acid Metabolism: Evidence for Secondary Insufficiency of 1-Carnitine (R. A. Chalmers, C. R. Roe, T. E. Stacey, and C. L. Hoppel, PEDIATRIC RESEARCH. pp 1325-1328, Vol. 18, No. 12, 1984).

As part of the original writing by the inventors, the 'Newborn Screening' test, which was run on the patient when she was 3 years old and filed as a document in our original writing, revealed the following:

Newborn Screen (Carnitine profile) drawn on Feb. 8, 2001
Free Carnitine=13 uM (Newborn Normal 20-280)
Total Acylcarnitine=10 uM (Newborn Normal 5-60)
Total Carnitine=23 uM (Newborn Normal 25-300)

Therefore, the patient's ratio of total acylcarnitine to total carnitine is:

$$\frac{\text{Total Acylcarnitine}}{\text{Total Carnitine}} = \frac{10}{23} = 0.4347826087$$

If a normal carnitine ratio is between 0.19 and 0.25 and ratio that is above 0.40 is considered abnormal, then the patient's ratio on Feb. 8, 2001, of 0.4347 is abnormal. As of Feb. 8, 2001, the parents of the patient were not active in the daily augmentation of the child with vitamins and supplements. Filed with the inventors original application is the very detailed appendix of all the supplements and vitamins that the parents were giving the patient as of the date of the filing of the original writing (in 2005), at which that time the parents were providing the child with daily supplementation with Carnitine.

Therefore, from direct experimentation one can see that before any supplementation, the 'Carnitine Ratio' of the patient was ABNORMAL (0.4348 on Feb. 8, 2001). Then, (documented in the Appendices of the inventors' original writing) after regular supplementation with Carnitine the 'Carnitine Ratio' was LOW (0.175 on Nov. 19, 2003. In the subsequent follow-up bloodwork recorded on Jan. 29, 2004, that documented the impact of the supplementation with exogenouse TML, the patient's 'Carnitine Ratio' was NORMAL (0.2326 on Jan. 29, 2004).

Consequently, the inventors have proven with direct experimentation that the therapeutic intervention with exogenous TML of sufficient purity can successfully intervene in a condition that involves a clinical impairment of carnitine or carnitine esters, or decreased fatty acid metabolism. Just as intervention with exogenous N-6-trimethyl-L-lysine was therapeutic in our patient, it may very well have therapeutic properties for the diseases outlined in the Abstract from 'Chalmers et al.' who suffer from disorders of organic acid metabolism which include, but are not limited to: Propionic Acidemia, Methylmalonic Aciduria, Isovaleric Acidemia, Multicarboxylase Deficiency, 3-hydroxy-3-methylglutaric aciduria, Methylacetoacetyl-CoA thiolase deficiency, and various dicarboxylic acidurias including glutaric aciduria, medium-chain acyl-CoA dehydrogenase deficiency and multiple acyl-CoA dehydrogenase deficiency.

Fatty Acid Metabolism and Low ATP Production

What could we do to provide enough ATP in the above transaction (in an LINCL child)? Enter TML. Earlier, we noted that TML as the first of four metabolites in the carnitine biosynthesis pathway. If TML is not being synthesized in the body as previously hypothesized, then carnitine cannot be endogenously synthesized. If carnitine is not available (and for the sake of our discussion, endogenous carnitine, since all four of the metabolites in the carnitine biosynthesis pathway reside in the brain), then appropriate oxidative phosphorylation (fatty acid oxidation) is not going to be efficient, if at work at all. If oxidative phosphorylation is not operating properly, then its end product will be deficient, or virtually absent. This end product is ATP.

Glutamine, Clinical Hyperammonemia, and Pyruvate Levels

Typically, LINCL afflicted children get to a point in the disease continuum that they do not know day from night because of the degree of affect the disease has had on the brain stem. It is of more than just interest to note that those who are taking glutamine as a supplement for sports performance enhancement or to combat aging can experience "nervousness" and "insomnia" if the dose is too large. Glutamine by itself is not "excitatory." But Glutamine supplementation will cause the synthesis of glutamate, which is an excitatory neurotransmitter ("*Escherichia coli* and *Salmonella*," Cellular and Molecular Biology, 2nd Edition, American Society for Microbiology, Washington, D.C., 1996). The Glial cells (Astrocytes) are responsible for ridding the extracellular space of extra Glutamate. However, the conversion of Glutamate into Glutamine is a "one-way" pathway that is ATP dependent (Nucleic Acids Res. 30(1):59 2002 (see Schematic 2). In fact it looks like this:

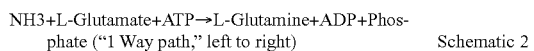

NH3+L-Glutamate+ATP→L-Glutamine+ADP+Phosphate ("1 Way path," left to right)　　　Schematic 2

There are two very important items of note in this experiment. First, if there is not enough ATP, then this transaction is unable to be completed. Second, if this transaction is not completed in the extracellular space, two items will remain in the extracellular space, Ammonia (NH3) and Glutamate. If too much NH3 accumulates then ultimately a state of "Hyperammonemia" will result (similarly to what was seen in the child). It is interesting to note that "[t]he conversion of glutamic acid into glutamine is the only means by which ammonia in the brain can be detoxified" ("Prescription For Nutritional Healing," 3rd edition, Phyllis A. Balch, CNC and James F. Balch M.D. p. 47, Avery Publishing, New York, 2000). If too much Glutamate accumulates in the extracellular space, then there will be too much "excitatory" neurotransmitter. In sports supplementation mentioned above this may just be "nervousness." In a LINCL child who is already neurologically compromised, this may manifest itself as myoclonus.

We have seen that if there is deficient/absent ATP, then glutamate will not be converted to glutamine and excess glutamate and ammonia will be the result. We believe that the results of amelioration of insomnia (clearing of glutamate), amelioration of hyperammonemia (clearing of ammonia) and the normalization of the glutamine level (a by product of high ammonia levels in the blood) and the overall glutamine/glutamate metabolism seems to be the direct result of TML therapy on the level of available ATP.

As noted in Table A, above, the patient's baseline glutamine reading prior to administration of TML was 99 (high). After the administration of TML the follow-up bloodwork showed a reading of 70 (normal!). Thus, the TML therapy showed a marked decrease in glutamine levels.

After the administration of TML, amelioration of the hyperammonemic condition witnessed by us (blue hands and feet) and in the clinical notes of the examining physician of Children's Hospital, who noted the clinical condition in his review of the blood work ("alanine is elevated, this may be seen in states with increased pyruvate, glutamine is increased, this may be seen with hyperammonemia. Clinical correlation is indicated"). Just as we saw her hands and feet return to normal coloration, the physician noted. Thus, as was hypothesized, administration of TML affected the carnitine levels, which in turn affected ATP production, glutamine/ammonia levels, and pyruvate levels.

While the present invention has been particularly described in terms of certain preferred embodiments, the invention is not limited to such preferred embodiments. The scope of the invention is broader and includes conditions susceptible to deficiencies in the TML pathway, including decreased fatty acid metabolism and lower energy production/ATP synthesis, clinical hyperammonemia, and a clinical state of impairment of carnitine or carnitine esters.

We claim:

1. A method of treating a human being for a condition associated with a deficiency in the N-6-trimethyl-L-lysine (TML) pathway affecting biosynthesis of carnitine, by administration of a pharmaceutically acceptable salt of N-6-trimethyl-L-lysine (TML) or TML derivative, wherein said condition involves a clinical state of impairment of carnitine or carnitine esters, or decreased fatty acid metabolism.

2. The method of claim 1, wherein said pharmaceutically acceptable salt of N-6-trimethyl-L-lysine (TML) or TML derivative is of at least 98% purity.

* * * * *